United States Patent [19]
Guala

[11] Patent Number: 4,895,167
[45] Date of Patent: Jan. 23, 1990

[54] URINE COLLECTING AND HOLDING DEVICE FOR DELIVERY TO ANALYTICAL LABORATORIES

[75] Inventor: Piergiacomo Guala, Alessandria, Italy

[73] Assignee: Sta.te. S.p.A., Alessandria, Italy

[21] Appl. No.: 295,912

[22] Filed: Jan. 10, 1989

[30] Foreign Application Priority Data

Oct. 10, 1988 [IT] Italy ................. 22245 A/88

[51] Int. Cl.⁴ ............................................. A61B 5/00
[52] U.S. Cl. ..................................... 128/760; 604/317
[58] Field of Search ....................... 128/760, 763, 767; 604/51, 54, 55, 317, 326, 349

[56] References Cited

U.S. PATENT DOCUMENTS 3,723,040 12/1975 Beach ................................. 128/760
4,393,881 7/1983 Shah ................................... 128/760
4,557,274 12/1985 Cawood .............................. 604/349
4,761,379 8/1988 Williams et al. .................... 128/760
4,805,635 2/1989 Korf et al. ........................... 128/763

Primary Examiner—Max Hindenburg
Attorney, Agent, or Firm—Notaro & Michalos

[57] ABSTRACT

A device for collecting and holding urine, for use in analytical laboratories, comprises a cylindrical, test tube-shaped container, a stopper fitted to the container and having a body which is through-penetrated coaxially by a first passageway and off-centrally by a second passageway, a funnel-shaped member having an outlet mouth fitted to the first passageway, a thin tube fast with the stopper at the second passageway and extending toward the bottom of the container as far as a predetermined distance off said bottom, a mount formed between the outlet mouth and the first passageway, for univocally oriented application of the mouth fitting to the passageway, and a closure element for said passageways connected to the stopper by means of a hinge.

This device enables collection of a strictly constant amount of urine between individual devices.

4 Claims, 2 Drawing Sheets

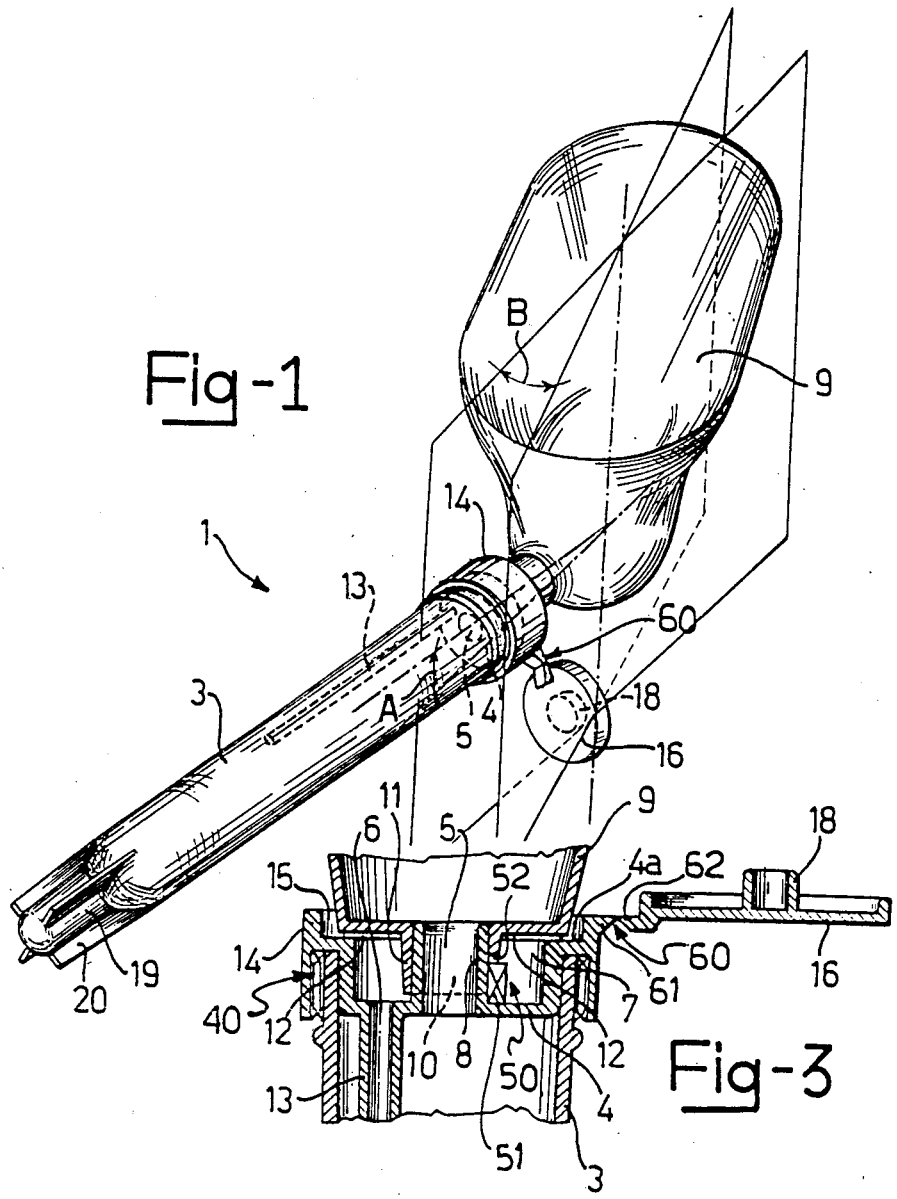
Fig-1
Fig-3
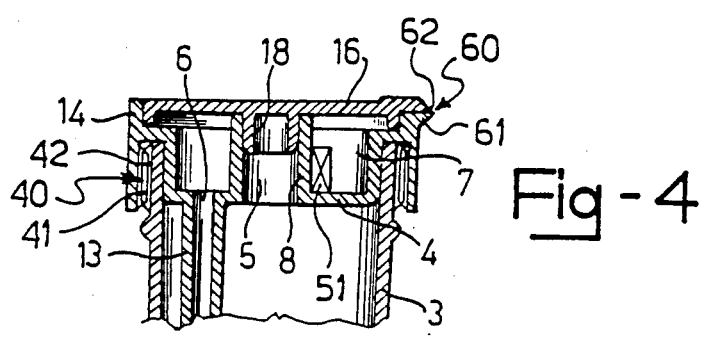
Fig-4

URINE COLLECTING AND HOLDING DEVICE FOR DELIVERY TO ANALYTICAL LABORATORIES

DESCRIPTION

This invention relates to a device for collecting and holding urine for use in analytical laboratories.

Urine test is one of the most frequently performed laboratory tests. It is restored to, in fact, every time that a complete picture of the general clinical state of an individual is to be provided, or whenever required by some specific situation, such as testing for pregnancy.

In order to carry out a urine test, a sample of one's urine has to be collected and taken to an analytical laboratory. To accomplish this, some devices are known which are the outcome of studies by this same Applicant (Italian Patent Application 21801-B/81; UK Patent 2098487).

Such prior devices, conceived for mass production and to be disposable after use, are in many ways advantageous but beset with the drawback that the amount of the collected urine cannot be a strictly constant one, and may vary between individual devices.

The problem underlying this invention is to provide a device of the type specified above which can collect and hold urine to be taken to an analytical laboratory in amounts which do not vary between individual devices.

This problem is solved by a device as indicated being characterized in that it comprises a cylindrical test tube-shaped container, a stopper fitted to the container and having a body through-penetrated coaxially by a first passageway and off-centrally by a second passageway, a funnel-shaped member having an outlet mouth fitted to the first passageway, a thin tube attached to the stopper, at the second passageway, and extending toward the container bottom as far as a predetermined distance off said bottom, a mount formed between the outlet mouth and the first passageway, for application of the mouth fitting in an oriented fashion to the passageway, and a closure element for said passageways connected to the stopper by a hinge.

Further features and the advantages of the device according to this invention will be more clearly understood from the following detailed description of a preferred embodiment thereof, to be taken by way of illustration and not of limitation in conjunction with the accompanying drawings, where:

FIG. 1 is a perspective view of a device according to the invention, ready for collecting urine to be forwarded to an analytical laboratory;

FIGS. 3 and 4 are enlarged scale sectional views of a detail of the device shown in FIG. 2, at two different stages of its use.

Figure 2:
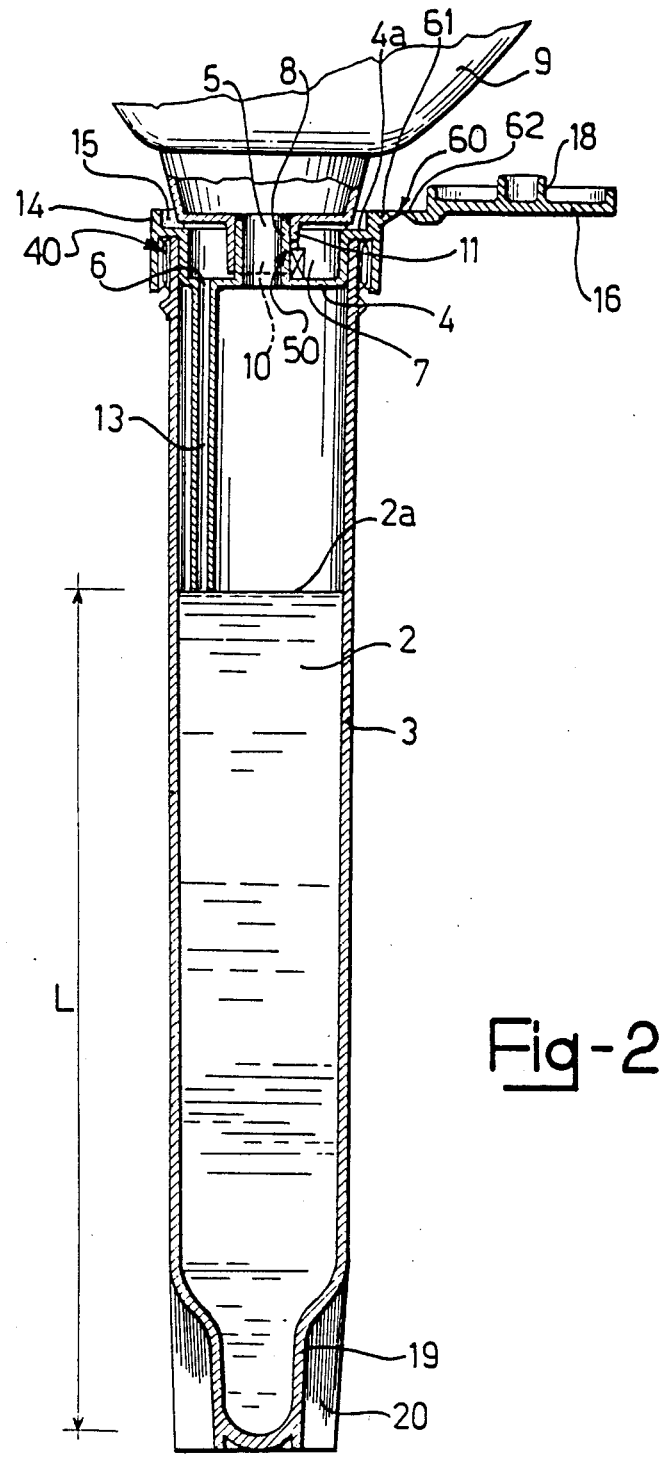
FIG. 2 is a sectional view of the device shown in FIG. 1.

With reference to the drawing views, the numeral 1 comprehensively designates a device according to the invention for collecting and holding urine 2 to be forwarded to analytical laboratories.

The device 1 comprises a cylindrical test tube-shaped container 3, advantageously made of a transparent plastics material, e.g. polystyrene, and a stopper 4 for said container 3 which is fitted detachably to the container 3. The stopper 4, which is formed from a plastics material such as a polyethylene resin, is secured on the container 3 as by a threaded connection 40 which comprises an outside thread 41 formed on the container 3 and an inside thread 42 formed in the stopper 4. It is of advantage that the threads, 41 and 42, are configured to permit of the stopper 4 to be applied on the container 3 in an axial fit relationship.

The stopper 4 has a body which is through-penetrated coaxially by a first cylindrical passageway 5 and off-centrally by a second cylindrical passageway 6, and is formed with an annular chamber 7 which is coaxial with the passageway 5 and defines a tubular portion 8.

The passageway 6 also opens into the annular groove 7.

The cross-sectional area of the passageway 5 has a predetermined limited value, tied to the length dimension of the passageway, thereby providing for the formation of a stable urine meniscus upon turning the container upside down.

The device 1 further comprises a funnel-shaped member 9. The member 9 is advantageously made of a plastics material, such as polypropylene. The funnel-shaped member 9 has an outlet mouth 10 adapted to fit over the first passageway 5. In particular, the outlet mouth 10 of the funnel-shaped member 9 is bordered by a tubular portion 11 which is intended to be a tight fit on the tubular portion 8.

Formed between the outlet mouth 10 and the first passageway 5 is a mount 50 for applying the mouth 10 to the passageway 5 in an oriented fashion.

The mount 50 comprises a single projection 51 formed in the passageway 5, specifically at a generatrix line of the tubular portion 8, and a single recess 52 formed inside the outlet mouth 10, specifically at a generatrix line of the tubular portion 11.

The shape of the recess 52 matches that of the projection 51, thereby it can be engaged by the latter in close clearance fit relationship therewith.

The funnel-shaped member 9 bears on the top wall 4a of the stopper 4 via upstanding radial ribs collectively indicated at 12.

At the second cylindrical passageway 6, the stopper 4 carries a thin tube 13 rigidly therewith which is formed from a like material and extends toward the bottom of the container 3 as far as a predetermined distance L off said bottom.

The stopper 4 has at the top a small annular molding 14, defining a seat 15 which has diameter annd depth dimensions which are the equal of the diameter and thickness of a disk 16, so that it can receive the disk 16 irreversibly in tight sealed relationship. Accordingly, the disk 16 will constitute a closure element for the passageway 5 and 6. The disk 16 is made of the same material as the stopper 4 and is connected thereto by a hinge 60.

The hinge 60 advantageously comprises a stiff bridge 61, extending between the stopper 4 and the disk 16, and a norrowing cross-section, virtually punctiform, portion 62 is formed along said stiff bridge, specifically at its midlength, which constitutes the hinge pivot.

The disk 16 is provided at its center with a tubular portion 18, so dimensioned as to fit tightly within the tubular portion 8 as the disk 16 is inserted into the seat 15.

For reasons to become apparent hereinafter, the outlet mouth 10 of the funnel-shaped member is positioned such that, when the funnel-shaped member occupies its operative position flare upwards (see FIG. 1), the axis of the outlet mouth 10, and hence the axis of the container 3, lie along a direction forming an angle A from horizontal. That angle A is selected to be approximately 30 degrees.

In addition, the funnel-shaped member 9 is an oblate shape, such as to be flattened in a vertical plane forming and angle B with a vertical plane led through the container 3. That angle B is selected to be approximately 30 degrees.

The projection 51 and recess 52 are located such that the mount 50 can provide for a univocally oriented fit of the outlet mouth 10 over the passageway 5, and accordingly, of the funnel-shaped member 9 over the container 3.

In accordance with that univocal orientation, and with reference to said operative position of the device wherein the funnel-shaped member has its flare up, the thin tube 13 locates in said vertical plane above the axis of the container 3.

The cylindrical container 3 has a bottom portion, indicated at 19, formed with a narrowing cross-section portion and with radial stiffening ribs 20.

The external configuration of the cylindrical container 3, and specifically its overall length and cross-section, are so dimensioned as to allow the container to be used on a laboratory centrifuge of conventional design.

The operation of the inventive device will be next described in relation to a starting condition as shown in FIG. 1.

The (male or female) patient whose urine is to be tested should hold the device such that, as shown in FIG. 1, the funnel-shaped member has its flare up. The patient will then be able to discharge his/her urine into the funnel at least until liquid settles at the funnel bottom. Due to the container 3 being set at an angle A from horizontal (in an arrangement that reduces the overall height of the complete device) and to the container being set at an angle B to the oblation plane of the funnel-shaped member, the device can be readily used over a bidet by a female patient, by holding it at the container.

The urine will flow from the funnel 9 into the container 3 through the outlet mouth 10 and the passageway 5, while a corresponding volume of air is vented out of the container 3 through the thin tube 13, annular groove 7, and the interspace maintained by the ribs 12 between the top wall 4a of the stopper 4 and the funnel-shaped member 9.

Upon the level 2a of the urine 2 in the container 3 reaching the free end of the tube 13, any further venting of air out of the container 3 is inhibited, and as a consequence, the transfer of urine from the funnel-shaped member 9 into the container 3 interrupted. Thus, the container 3 will be filled to contain the exact amount of urine sought.

At this stage, the user should turn the device upside down, and pour out urine left at the bottom of the funnel-shaped member 9. During this operation, no urine can flow out of the container 3 due to the formation of a stable liquid meniscus at the passageway 5.

After discarding the excess urine, the user should tear the funnel-shaped member 9 off the container 3 and discard it; thereafter, the user should turn the disk 16 about the hinge 70 until it fits tightly into the seat 15.

Thus, the container 3 has been sealed and can be forwarded to the analytical laboratory, where it will be unsealed according to necessity, by just unscrewing the stopper 4 and without this involving removal of the disk 16, not even unintentionally.

By virtue of its outward configuration, the container can installed directly on the centrifuge.

In the course of the test, sediments will settle at the bottom of the container 3 in the narrowing cross-section tubular portion 19.

A major advantage of the device according to the invention is that it can ensure collection of a strictly constant amount of urine between individual devices, thanks to the thin tube, which controls the top level of the urine within the container, occupying invariably the same position in all devices.

The inventive device has also shown to be easily handled. In fact, the funnel-shaped member can be readily removed by just tearing it off, the container positively retaining its stopper on account of its threaded engagement therewith. Further, the closure element can also be readily applied to the stopper to seal the container, inasmuch as the precision fit of the disk to the molding is ensured by its precision pivotal movement abou the hinge.

Understandably, a skilled person in the art may select to alter and modify the device just described in many ways to meet individual contingent demands, without departing from the true scope of the invention as set forth in the appended claims.

I claim:

1. A device for collecting and holding urine for use in analytical laboratories, characterized in that it comprises a cylindrical test tube-shaped container, a stopper fitted to the container and having a body through-penetrated coaxially by a first passageway and off-centrally by a second passageway, a funnel-shaped member having an outlet mouth fitted to the first passageway, a thin tube attached to the stopper, at the second passageway, and extending toward the container bottom as far as a predetermined distance off said bottom, a mount formed between the outlet mouth and the first passageway, for application of the mouth fitting in an univocally oriented fashion to the passageway, and a closure element for said passageways connected to the stopper by a hinge.

2. A device according to claim 1, characterized in that said mount comprises a single projection formed in the passageway and a single recess formed in the mouth and matching in shape said projection.

3. A device according to claim 1, characterized in that it comprises a threaded connection of the stopper to the container.

4. A device according to claim 1, characterized in that said hinge comprises a stiff bridge extending between the stopper and the closure element, and a virtually punctiform narrowing cross-section portion formed along said bridge.

* * * * *